United States Patent [19]

Pruss

[11] Patent Number: 5,730,157
[45] Date of Patent: Mar. 24, 1998

[54] METHOD FOR TREATING VIRAL INFECTION

[75] Inventor: Thaddeus P. Pruss, Madison, Wis.

[73] Assignee: Clarion Pharmaceuticals Inc., Madison, Wis.

[21] Appl. No.: 749,417

[22] Filed: Nov. 15, 1996

Related U.S. Application Data

[60] Provisional application No. 60/008,351 Dec. 7, 1995.

[51] Int. Cl.$^6$ ..................................... A61B 19/00
[52] U.S. Cl. ......................... 128/898; 424/231.1
[58] Field of Search ............... 128/898; 424/229.1, 424/230.1, 231.1, 184.1

[56] References Cited

U.S. PATENT DOCUMENTS

| | | | |
|---|---|---|---|
| 4,372,949 | 2/1983 | Kodama et al. | |
| 4,650,791 | 3/1987 | Nomura et al. | |
| 4,859,769 | 8/1989 | Karlsson et al. | 514/25 |
| 4,980,462 | 12/1990 | Karlsson et al. | 536/53 |
| 5,116,992 | 5/1992 | Braquet et al. | |

OTHER PUBLICATIONS

Andreesen, R., "Ether Lipids in the Therapy of Cancer," *Prog. Biochem. Pharmacol.*, vol. 22, pp. 118–131 (Kaeger, Basal 1988).

Brachwitz et al, *Chemistry and Physics of Lipids*, vol. 31, pp. 33–52 (1982).

Hermetter, A. and Paltauf, F., Procedures for the Synthesis of Ether Lipids, in H.K. Mangold and F. Paltauf, *Ether Lipids*, Academic Press (1983), p. 393 et.seq.

Paltauf, F. and Hermetter, A., *Methods Enzymol.*, vol. 197, pp. 134–149 (1991).

*Primary Examiner*—Vincent Millin
*Assistant Examiner*—Kelly R. O'Hara
*Attorney, Agent, or Firm*—DeWitt Ross & Stevens S.C.

[57] ABSTRACT

The present invention relates to the treatment and prophylaxis of viral infections with fatty alkyl and alkenyl ether glycerophosphoethanolamines bearing a 3-(2-imidazolinyl)-2-imidazolinyl or 2-imidazolinyl substituent on the ethanolamine nitrogen.

10 Claims, No Drawings

METHOD FOR TREATING VIRAL INFECTION

RELATED APPLICATION DATA

This application claims the benefit of U.S. Provisional application Ser. No. 60/008,351 filed Dec. 7, 1995.

TECHNICAL FIELD

The present invention relates to the treatment and prophylaxis of viral infections with novel N-substituted glycerophosphoethanolamines.

BACKGROUND OF THE INVENTION

The use of synthetic fatty alkyl and alkenyl ether glycerophospholipids for the treatment of certain diseases has been reported in the literature. See, for example, F. Paltauf, Chem. Phys. Lipids 74, 101–139 (1994). The compound 1-O-octadecyl-2-O-methyl-sn-glycero-3-phosphocholine (ET 18-OCH$_3$) has markedly potent anti-tumor activity. See R. Andreesen, "Ether Lipids in the Therapy of Cancer," Prog. Biochem. Pharmacol. 22, 118–131 (Karger, Basel 1988). Treatment of cancer with a fatty alkyl ether glycerophosphoethanolamine compound is also disclosed in U.S. Pat. No. 4,372,949. Halo substituted cytostatic analogs are described by H. Brachwitz et al., Chemistry and Physics of Lipids 31, 33–52 (1982). Glycerophospholipids bearing a $C_{10-24}$ alkyl ether substituent in the 1-position, a cyclic amido group in the 2-position, and a cyclic ammonio group as part of the phosphoethanolamino function in the 3-position of the glyceryl backbone are described in U.S. Pat. No. 4,650,791. Also disclosed in U.S. Pat. No. 4,650,791 are synthetic intermediates wherein the substituents are as described in the preceding sentence herein except that there is an hydroxyl group at the 3-position or hydroxyl groups at both the 1-position and the 3-position of the glyceryl backbone. Glycerophosphoethanolamines bearing a non-cyclic, substituted amino substituent in the 2-position and a lower $C^{1-5}$ alkyl ether substituent in the 1-position of the glyceryl backbone are disclosed in U.S. Pat. No. 5,116,992.

SUMMARY OF THE INVENTION

The present invention relates to the use of novel N-substituted glycerophosphoethanolamines and pharmaceutically acceptable salts thereof to treat, control or prevent viral infections.

More specifically, the invention provides a method of treating a susceptible viral infection in a mammal which comprises administering to said mammal an anti-virally effective amount of an N-substituted glycerophosphoethanolamine or a pharmaceutically acceptable salt thereof described in the commonly owned, co-pending U.S. Patent Application bearing the title "N-substituted Glycerophosphoethanolamines" and Attorney Docket No, 43549/199. The N-substituted glycerophosphoethanolamines, to which the invention of this Application relates, comprise fatty alkyl or alkenyl ether glycerophosphoethanolamines bearing a 3-(2-imidazolinyl)-2-imidazolinyl or 2-imidazolinyl substituent on the ethanolamine nitrogen.

DETAILED DESCRIPTION OF THE INVENTION

The present invention provides a method for treating viral infections by administering to an infected mammal an anti-virally effective amounts of a N-substituted, fatty alkyl or alkenyl ether glycerophosphoethanolamine having a 2-imidazolinyl substituent on the ethanolamine nitrogen, or a pharmaceutically acceptable salt thereof. The subject compounds are represented by the general Formula I:

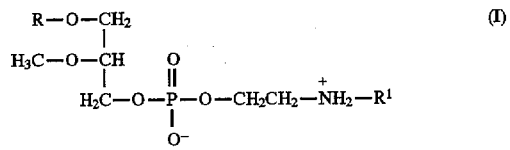

wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and $R^1$ is 3-(2-imidazolinyl)-2-imidazolinyl or 2-imidazolinyl.

The invention encompasses the use of all of the optical and geometric isomers of the compounds of Formula I as well as the pharmaceutically acceptable salts of the compounds of Formula I and of said isomeric forms thereof.

The subject compounds, wherein $R^1$ is 3-(2-imidazolinyl)-2-imidazolinyl, are represented by Formula Ia:

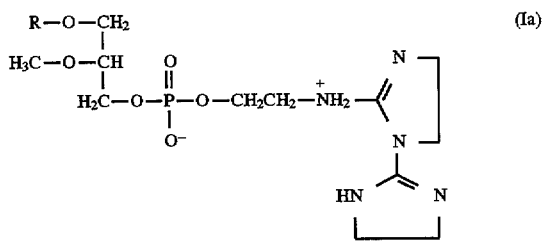

The subject compounds wherein $R^1$ is 2-imidazolinyl are represented by Formula Ib:

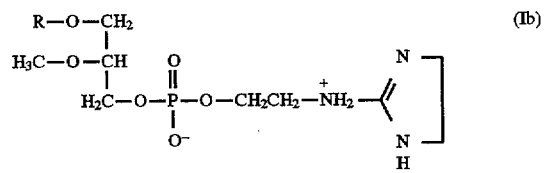

As used herein, R is selected from the group consisting of (1) substituted or unsubstituted, preferably unsubstituted, $C_{14-20}$ alkyl groups, preferably $C_{16-18}$ alkyl, such as, for example, tetra-, penta-, hexa-, hepta-, octa-, nonadecyl-, eicosyl-, or the branched analogs thereof; and (2) substituted or unsubstituted, preferably unsubstituted, $C_{14-20}$ alkenyl groups, preferably $C_{16-18}$ alkenyl, whereby a double bond of the alkenyl group does not involve the carbon atom of said alkenyl that is bonded to the oxygen of the glyceryl backbone. Both the aforementioned alkyl and alkenyl groups can be substituted at one or more carbons, preferably at one, with substituents which do not interfere with syntheses of the compounds during the synthetic steps of making them. Preferred substituents are halo, $C_{1-3}$ alkoxy or cyano. The term "halo" refers to any of the four halogens, chloro, bromo, iodo and fluoro, with chloro and fluoro being preferred.

The preferred Formula I compounds are the following:

1-O-n-octadecyl-2-O-methyl-glycero-3-phospho-N-[3-(2-imidazolinyl)-2-imidazolinyl]-ethanolamine, also referred to as CPR-3003;

1-O-n-octadecyl-2-O-methyl-glycero-3-phospho-N-(2-imidazolinyl)-ethanolamine, also referred to as CPR-3004;

1-O-n-hexadecyl-2-O-methyl-glycero-3-phospho-N-[3-(2-imidazolinyl)-2-imidazolinyl]-ethanolamine; and 1-O-n-hexadecyl-2-O-methyl-glycero-3-phospho-N-(2-imidazolinyl)-ethanolamine.

Other particular compounds of Formula I are those wherein R is n-tetradecyl, n-eicosyl, 9-hexadecenyl, 9-octadecenyl, 2-chloro-n-octadecyl, 2-methoxy-n-octahexyl, 2-cyano-n-hexadecyl, cis- or trans-9-octadecenyl and cis- or trans-9-hexadecenyl.

The Formula I compounds have an asymmetric carbon atom (C2 position in the glyceryl backbone) in their structures. Consequently these compounds may exist in the form of different R and S optically isomeric forms (enantiomers) or racemates. Substantially pure forms of either of the R- and S-isomer may be obtained, substantially free of the other, by the application of art-known resolution methodologies such as, for example, column chromatography using chiral columns or starting the preparation from the R- or S-isomer of an appropriate precursor. Unless otherwise specified, the compounds, the use of which is described in the examples, are in racemic form.

In addition, cis- and trans-geometric isomers may also be present in the subject compounds, e.g., when R in Formula I is $C_{14-20}$ alkenyl, due to the cis- and trans-configuration inherent with the double bond. Thus, by initially starting with an appropriate cis- or trans-precursor, the corresponding end-product of the Formula I compound will be obtained.

A reference herein to a compound of Formula I (or I(a) or I(b)) is to all optical/enantiomeric and all geometric isomers thereof, unless the reference is otherwise qualified.

The anti-viral use of all isomeric forms of the Formula I compounds, including pure enantiomeric and geometric isomers and mixtures thereof, is intended to be within the scope of this invention.

The salts of the compounds of Formula I, the use of which is within the scope of the invention, are pharmaceutically acceptable salts and include acid addition salts, such as, for example, those made with hydrochloric, hydrobromic, nitric, sulfuric, phosphoric, carbonic, acetic, citric or lactic acids, as well as salts made with bases, such as, for example, sodium hydroxide, potassium hydroxide or calcium hydroxide. The salts of the invention are made by conventional methods well known to the skilled.

The compounds of the present invention may be prepared by the stepwise procedures outlined in the following reaction scheme, wherein Tr is triphenylmethyl (trityl) and Me is methyl, and the subsequent examples. The compounds produced by the reaction scheme may be purified by conventional methods of the art, e.g., chromatography, recrystallization, etc.

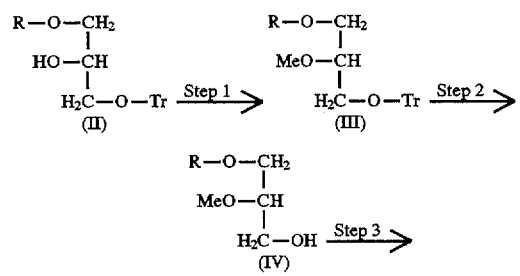

-continued

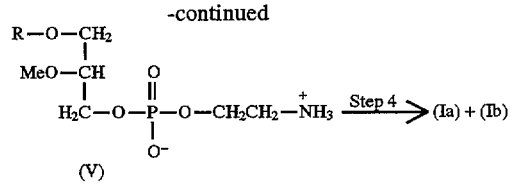

Step 1

The compounds of Formula II are known in the literature or can be obtained by art-recognized procedures. See, for example, A. Hermetter and F. Paltauf, Procedures for the Synthesis of Ether Lipids, p. 393 et.seq., in H. K. Mangold and F. Paltauf, "Ether Lipids", Academic Press, 1983, and F. Paltauf and A. Hermetter, Methods Enzymol. 197, 134–149 (1991). Also see Examples 1–3 which follow. Treatment of (II) under an inert atmosphere with potassium t-butylate and dimethylsulfate in an inert aprotic solvent such as toluene at elevated temperatures yields the corresponding 2-methoxy compound, 1-O-R-2-O-methyl-3-O-trityl-glycerol (Formula III), also known as methyl-trityl-batylalcohol when R=n-octadecyl.

Step 2

Removal of the trityl function in compound (III) to yield 1-O-R-2-O-methyl-glycerol (Formula IV), also known as methyl-batylalcohol when R=n-octadecyl, is readily accomplished by art-recognized procedures, e.g., by reacting a cooled solution (15°–18° C.) of (III) in an inert aprotic solvent such as n-hexane with gaseous HCl.

Step 3

The phosphoethanolamine moiety is introduced by reaction of the hydroxyl in (IV) with POCl$_3$ and triethylamine at low temperatures (0°–4° C.) in an anhydrous solvent such as tetrahydrofuran, followed by reaction with ethanolamine, and treatment with aqueous dilute hydrochloric acid, to yield 1-O-R-2-O-methyl-glycero-3-phosphoethanolamine (V).

Step 4

To a suspension of (V) in an appropriate organic solvent, e.g., isopropanol, S-methyl-N,N'-ethylene-isothiourea is added and the mixture refluxed for several hours. After cooling to room temperature, the solvent is evaporated off. Water is added and the pH adjusted to about 4 with HCl solution. Conventional workup affords approximately equal amounts of the corresponding 3-(2-imidazolinyl)-2-imidazolinyl (Formula Ia) and 2-imidazolinyl (Formula Ib) compounds which are readily separated by conventional chromatographic techniques.

Working up the individual stepwise products indicated in the reaction scheme is advantageously carried out by standard methodologies, for example, by evaporating solvent from the reaction solution or precipitating the product from the reaction solution by dilution of the solution with an appropriate antisolvent (a solvent in which the product is less soluble than in the solvent of the reaction solution). The crude intermediate products obtained may be quite suitable, without further purification operations, for the preparation of the final products, which then may be purified. Particularly suitable methods for purifying the Formula I compounds are the conventional chromatographic methods, such as preparative thin-layer chromatography (TLC), column chromatography, adsorption chromatography, medium pressure liquid chromatography (MPLC) or high pressure liquid chromatography (HPLC).

The anti-viral activity of the above-described compounds of Formula I and pharmaceutically acceptable salts thereof may be assayed by many ways conventional in the art. Two of these assays are described here. The first assay measures inhibition of cytopathic effects (CPE) caused by viral infection of the cells, and the second assay is a standard viral yield reduction assay. This yield reduction assay is a modification of the general method described by Erlich et al. (Ann. NY Acad. Sci. 1965, 130, 5–16). These two assays demonstrate the marked anti-viral activity of the subject compounds, including salts.

No cytotoxicity has been observed with the compounds of Formula I or pharmaceutically acceptable salts thereof at anti-virally effective levels.

The anti-viral agents of the present invention (the compounds of Formula I and the pharmaceutically acceptable salts thereof) are particularly effective for the treatment of an infection by Herpes viruses (particularly both immunologically defined types of Herpes simplex, HSV-1 and HSV-2), and Poliomyelitis virus (including all three immunologically distinguishable types thereof), although infections caused by other viruses, such as, for example, Varicella-zoster virus, Togaviruses, Cytomegalovirus (CMV), Epstein-Barr virus (EBV), Picornaviruses, Rhinovirus, Human papillona viruses and Hepatitis viruses, among others, may also be effectively treated.

The anti-viral agents of the present invention are suitable for application to mammals (such as human beings, horses, cattle, dogs and rodents). The route of administration is usually oral or parenteral, although it is possible to administer the anti-viral agents by other administration routes, e.g., by topical application, depending on whether the preparation is used to treat internal or external viral infections, or nasal application. Topical application can be used for systemic treatment.

The anti-viral agents of the invention are to be administered under the guidance of a medical or veterinary professional. The daily dose and dosage regimen may vary depending upon, e.g., the virus involved in the infection, the species of mammal infected by the virus, the sex, age, body weight and general medical condition of the individual mammal being treated, the type of formulation or dosage form being administered, and the route of administration. The daily dose and dosage regimen are ultimately at the discretion of the medical or veterinary practitioner.

However, a suitable effective dose of the anti-viral agent is in the range of about 0.5 to about 500 mg/kg body weight per day, preferably in the range of about 1 to about 300 mg/kg body weight per day, of compound of Formula I. (If the agent is a salt of a compound of Formula I, the dose is determined on the basis of the mass of compound of Formula I in the salt.) The total daily dose, for example, may be given as a single dose or multiple doses, e.g., two to six times per day, or by intravenous infusion for a selected duration. Dosages above or below the cited range are within the scope of the present invention and, as desired or determined to be necessary by the medical or veterinary professional, may be administered to a mammal being treated.

Effective unit dosage forms containing, for example, from about 0.5 to about 500 mg of compound of Formula I (per se or as part of a pharmaceutically acceptable salt) per unit dosage are suitably employed. As used herein, the term "effective unit dosage" or "effective unit dose" means a predetermined anti-viral amount sufficient to be effective against the viral organism in vivo, and "unit dosage form" includes a discrete dosage unit such as a capsule, tablet, teaspoonful or the like.

It is noted that the Formula I compounds typically decompose on heating above about 200° C. This characteristics may need to be taken into consideration in, for example, preparing tablets on a commercial scale where the heat of compression may be a factor. The Formula I compounds are also rather insoluble in water and, accordingly, liquid formulations which account for this factor may be made according to art-recognized pharmaceutical techniques, for example, an injection wherein the active compound is dissolved in a suitable solvent or co-solvent such as an appropriate polyethylene glycol, or a propylene glycol or the like, or a sealed gelatin capsule enclosing an oily solution of the active compound, or suppository base such as cocoa butter, or a liposome formulation, for example, the active compound and a glycerophospholipid such as phosphatidylcholine. In any event, the aforementioned characteristics of the Formula I compounds are not uncommon in the pharmaceutical area and, accordingly, art-recognized pharmaceutical techniques are employed to prepare appropriate formulations for such compounds as those of Formula I, isomers thereof, or pharmaceutically acceptable salts of either.

The formulations may conveniently be presented in unit dosage form and may be prepared by any of the methods well known in the art of pharmacy. All methods include the step of bringing the active compound or salt into association with a pharmaceutically acceptable carrier plus one or more optional accessory ingredients utilized in the art of pharmaceutical formulations, e.g., diluents, buffers, flavoring agents, binders, surfactant, thickeners, lubricants, preservatives and the like. In general, the formulations are prepared by uniformly and intimately bringing the active compound into association with a liquid or solid carrier and then, if necessary, shaping or dividing the product into desired unit dosage form.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

Formulations suitable for parenteral administration conveniently comprise a sterile preparation of the active compound in, for example, a polyethylene glycol 200 or propylene glycol solution which is preferably isotonic with the blood of the recipient.

Useful formulations also comprise concentrated solutions or solids containing the compound of Formula I or a pharmaceutically acceptable salt or salts thereof which upon dilution with an appropriate solvent give a solution suitable for oral or parenteral administration.

In general, the pharmaceutical compositions of this invention contain from about 0.5 mg to about 500 mg and, preferably, from about 5 mg to about 350 mg of active ingredient (compound of Formula I per se or as part of a pharmaceutically acceptable salt), preferably in a unit dosage form, for each of the indicated activities of the invention.

The following examples are intended to illustrate and not to limit the scope of the present invention. Those of skill will recognize variations and modifications of what is described that are within the spirit of the invention. It is intended that the disclosed invention also entails such variations and modifications.

EXAMPLE 1

A. Octadecylmethanesulfonate

500 Grams (1.85 mol) of 1-octadecanol is suspended with stirring in 2500 ml methylene chloride and 224.5 g (2.22 mol; 310 ml) triethylamine is added with cooling (cold water). 254 Grams (2.215 mol; 171.5 ml) of methanesulfochloride dissolved in 500 ml methylene chloride is then added in such a way that the reaction temperature is maintained between 20° and 25° C. Stirring at ambient temperature is continued for 1.5 hours. The methylene chloride is removed under vacuum at a temperature of 35° C. maximum. To the remaining syrup 1000 ml of ethanol/water (1/1; v/v) are added and remaining methylene chloride is completely removed under vacuum. (Note: In the presence of even traces of methylene chloride, the product will not crystallize). An additional 2500 ml ethanol/water (1/1; v/v) is added with stirring. The resulting crystallizate is filtered off, washed three times with ethanol/water (1/1; v/v) and air-dried to yield 641 g (99.4%) of octadecylmethanesulfonate; m.p. 60°–61° C.; water content does not exceed 0.5%. B. By utilizing an equivalent amount of an appropriate $C_{14-20}$ alkanol or alkenol in the foregoing procedure, the following methanesulfonates are obtained:

n-tetradecylmethanesulfonate;

n-hexadecylmethanesulfonate;

n-eicosylmethanesulfonate;

cis-9-octadecenylmethanesulfonate;

trans-9-octadecenylmethanesulfonate;

cis-9-hexadecenylmethanesulfonate;

trans-9-hexadecenylmethanesulfonate;

2-chloro-n-octadecylmethanesulfonate;

2-methoxy-n-octadecylmethanesulfonate; and 2-cyano-n-hexadecylmethanesulfonate.

EXAMPLE 2

A. 1-O-n-Octadecyl-Glycerol (Batylalcohol)

In an argon atmosphere, 79.2 g (1.2 mol) powdered potassium hydroxide (purity 85%) is suspended in 1680 ml dimethylsulfoxide. 118.88 Grams (0.9 mol) solketal (rac-1, 2-isopropylidene-glycerol) is added and the mixture is stirred for one hour at ambient temperature (18°–23° C.). Stirring is continued and 209.16 g (0.6 mol) octadecylmethanesulfonate is added. Stirring is continued for another three hours and the reaction mixture is kept overnight at ambient temperature.

No argon atmosphere is necessary. A mixture of 840 ml methanol and 336 ml conc. HCl is added and the reaction mixture is refluxed with stirring for one hour. Stirring is continued for another two hours, followed by cooling the reaction mixture to 30° C. Then 1040 ml methanol is added and stirring is continued for 10 minutes. Upon keeping the reaction mixture at 4° C. overnight, a precipitate is formed which is filtered off and washed with 300 ml methanol/water (1:1; v/v) and 1000 ml water. The crude product is then suspended (without drying) in 6400 ml water and the suspension is vigorously stirred for 30 minutes. The precipitate is filtered off and washed with three portions of 500 ml water. The crystallizate is dried under vacuum over phosphorous pentoxide to yield 190 g (92%) of batylalcohol; m.p. 68°–70° C.

B. By substituting an equivalent amount of each methanesulfonate of Example 1-B for the octadecylmethanesulfonate of Example 2-A, each corresponding 1-O-R-glycerol is obtained.

EXAMPLE 3

A. 1-O-n-Octadecyl-3-O-Trityl-Glycerol (Tritylbatylalcohol) (Formula II)

51.69 Grams (150 mmol) of batylalcohol and 62.73 g (225 mmol) freshly recrystallized tritylchloride are dissolved at 35° C. in 350 ml methylene chloride. (Note: It is recommended that the tritylchloride be freshly recrystallized from halpasol, trademark for a petroleum ether fraction, b.p. 100°–120° C.). During 15 minutes, 22.77 g (225 mmol; 31.38 ml) triethylamine is added dropwise to the stirred solution at 30°–35° C. (cooling with a water bath). The reaction is continued for six hours at ambient temperature. (Note: It is recommended that a control TLC be done to make sure that the reaction is complete). The solution is then washed with 300 ml of a $NaHCO_3$ solution (1%), dried over anhydrous sodium sulfate, filtered and evaporated under vacuum. The oily residue (155 g) is dissolved in 660 ml acetonitrile by warming up to 70° C. with stirring. After cooling to room temperature the title product crystallizes (preferentially after adding a few seed crystals). Crystallization is completed by standing overnight at ambient temperature. The crystallizate is filtered off to yield 82.5 g (93.7%) of crude product (m.p. 53°–55° C.) which can be used for the following step without purification. Recrystallization from halpasol (310 ml) yields 71 g (80%) of pure tritylbatylalcohol. B. In a similar way, introduction of the 3-O-trityl function is accomplished for each 1-O-R-glycerol of Example 2-B.

EXAMPLE 4

1-O-n-Octadecyl-2-O-Methyl-3-O-Trityl-Glycerol (Methyl-Trityl-Batylalcohol) (Formula III)

Under an inert atmosphere (argon or nitrogen), 586.0 g (1 mol) trityl-batylalcohol (Formula II) and 112.2 g (1 mol) potassium-t-butylate are dissolved in 2000 ml toluene with stirring, heated to 85° C. and within 30 minutes 63.07 g (0.5 mol) dimethylsulfate (47.4 ml) are added. The temperature is raised to 100° C. and then the reaction mixture is refluxed for one hour. After cooling to 98° C., 112.1 g (1 mol) potassium-t-butylate and 63.07 g (0.5 mol) dimethylsulfate are added within 30 minutes while the mixture is refluxed. Refluxing with stirring is continued for 6 hours; then the mixture is kept overnight at room temperature. The mixture is extracted with water (3×2000 ml) and the organic layer is evaporated under vacuum to yield 620 g of the 1O-n-octadecyl-2-O-methyl-3-O-trityl-glycerol (methyl-tritylbatylalcohol) as an oily residue, which can be used in the following detritylation step without purification.

TLC:KG 60 F (Merck);

Mobile Phase: $CH_2Cl_2$; Rf: 0.20; Rf of an impurity (<5%) 0.02;

Visualized by iodine; (more sensitive visualization is achieved with chromate-sulphuric acid).

Pure methyl-trityl-batylalcohol Formula III can be obtained by MPLC:

Apparatus: Waters PREP 500;

2 Silica cartridges (equals approx. 800 g silica, normal phase);

Mobile Phase: $CH_2Cl_2$;

Sample: 15 g raw (Formula III) dissolved in 30 ml $CH_2Cl_2$;

Axial Pressure: 38 bar;

Internal Pressure: 9–15 bar;

Flow Rate: 200 ml/min;
Detection: RI-detector; Split 1:100

EXAMPLE 5

1-O-n-Octadecyl-2-O-Methyl-Glycerol (Methyl-Batylalcohol) (Formula IV)

616.3 Grams (calculated with impurities, 1 mol=600.9 G) of crude methyl-trityl-batylalcohol (Formula III) from Example 4 is dissolved in 1350 ml n-hexane and cooled to 15°–18° C. Within two hours 44 g (1.21 mol) gaseous HCl is passed into the stirred solution at the same temperature. After 30 minutes, tritylchloride starts to precipitate. The mixture is stirred for an additional hour at 15°–18° C. The precipitate is filtered off and washed with 250 ml cooled (16° C.) n-hexane. After air-drying, 214 g (76.76%) tritylchloride are obtained. The hexane phases are combined and kept at −20° C. overnight. The crystallized product is filtered off and washed with 220 ml cold (−20° C.) n-hexane. After air-drying, 331.35 g (92.4%) crude methyl-batylalcohol (Formula IV) are obtained. (Note: Depending on the amount of co-crystallizing trityl derivatives, the yield may exceed 100%. Another impurity is n-octadecanol which should be removed in any case because in the next reaction step it may form phospholipids that cannot be separated from the product.)

Purification: 500 Grams raw methyl-batylalcohol are dissolved in 1500 ml toluene and slowly filtered through a bed of 1500 g alumina on a glass frit. (Note: The alumina bed is prepared by filtering a slurry of alumina in toluene). The alumina is washed with 1500 ml toluene. The toluene phases are combined and evaporated to dryness under reduced pressure. Recrystallization from n-hexane at −20° C. yields 402.2 g methyl-batylalcohol (Formula IV) of sufficient purity to be used in the next step.

TLC:KG 60F (Merck);
Mobile Phase: $CH_2Cl_2$/EtOAc (4/1, v/v);
Rf: 0.40;
Visualized by iodine or by chromate-sulphuric acid.
Purification of raw methyl-batylalcohol by MPLC:
Steel column: 50×500 mm, Amicon (Grace);
Matrex silica: 20–45μ, normal phase (Grace);
Mobile phase: $CH_2Cl_2$/EtOAc (22/3; v/v);
Sample: 20.7 g raw (Formula IV) dissolved in 25 ml $CH_2Cl_2$;
Internal pressure: 8–12 bar;
Flow rate: 156 ml/min;
Detection: RI-detector or TLC;
Pure methyl-batylalcohol (Formula IV): m.p. 43°–44° C.

EXAMPLE 6

1-O-n-Octadecyl-2-O-Methyl-Glycero-3-Phosphoethanolamine (V)

A mixture of 40 ml anhydrous tetrahydrofuran (THF) and 36.8 g $POCl_3$ (240 mmol) is cooled to 0° C. Into this stirred solution, a mixture of 72 g (200 mmol) methyl-batylalcohol (Formula IV), 36.4 g (360 mmol) triethylamine and 240 ml THF is added dropwise as the temperature is maintained at 0°–4° C. Some material precipitates. The cooling device is removed and a mixture of 14.7 g (240 mmol) ethanolamine, 36.4 g (360 mmol) triethylamine and 180 ml THF is added to the stirred solution within 15 minutes. The temperature rises to about 55° C. and stirring is continued at this temperature for one hour. After cooling to 15° C., a mixture of 30 ml conc. HCl and 170 ml water is added at 25°–30° C. The reaction mixture is allowed to come to ambient temperature and stirring is continued for one hour. The water layer is removed and the THF layer is diluted with 600 ml methylenechloride. 50 grams of sodium bicarbonate are added with vigorous stirring. After continuing stirring for 15 minutes, anhydrous sodium sulfate is added and stirring is continued for a few minutes. The inorganic material is removed by filtration and the solvent is evaporated under reduced pressure. The honey-like residue is taken up in 500 ml methylene chloride and a slight turbidity is removed by adding charcoal followed by filtration over a glass filter. Half of the methylenechloride is distilled off and 200 ml acetone are added. Upon cooling to 0° C. for two hours, 91.2 g (94.7%) of raw product (V) precipitates. This material is dissolved in 800–900 ml boiling isopropanol. The solution is passed over a filter and cooled to room temperature. On standing overnight at room temperature 86.3 g (89.5%) of crystalline 1-O-n-octadecyl-2-O-methyl-glycero-3-phosphoethanolamine (V) is obtained.

TLC:KG 60 F (Merck);
Mobile phase 1: $CHCl_3$/$CH_3OH$/c. $NH_3$; 65/35/5 per vol.;
Rf: 0.22;
Mobile phase 2: $CHCl_3$/$CH_3OH$/acOH/HOH; 100/60/20/5 per vol.;
Rf: 0.18;
Visualized by chromate-sulphuric acid.
Purification of (V) by MPLC:
Steel column: 50×500 mm, Amicon (Grace);
Matrex silica: 20–45μ, normal phase (Grace);
Sample: 30 g (V) dissolved in 100 ml $CH_2Cl_2$ and 20 ml $CH_3OH$;
Internal pressure: 8–10 bar;
Flow rate: 78–156 ml/min;
Detection: RI-detector or TLC.

EXAMPLE 7

1-O-n-Octadecyl-2-O-Methyl-Glycero-3-Phospho-N-[3-(2-imidazolinyl)-2-Imidazolinyl]-Ethanolamine (CPR 3003) and 1-O-n-Octadecyl-2-O-Methyl-Glycero-3-Phospho-N-(2-Imidazolinyl)-Ethanolamine (CPR 3004).

To a suspension of 9.63 g (20 mmol) of 1-O-n-octadecyl-2-O-methyl-glycero-3-phosphoethanolamine (V) in 300 ml isopropanol, 9.3 g (80 mmol) of S-methyl-N,N'-ethylene thiourea are added and the mixture is refluxed for six hours. After standing overnight at room temperature, the solvent is evaporated under vacuum. Water (150 ml) is added to the residue and the pH of the suspension is brought to 4 by addition of approximately 14 ml 4N HCl. The gelatinous suspension is extracted with two portions of chloroform-:methanol (2:1, v/v) and the organic phase is dried over anhydrous sodium sulphate. The sodium sulphate is then filtered off and the solvent is removed under vacuum. The residue is stirred overnight with 150 ml diethylether. The solid product is filtered off and air-dried to yield 12 g of crude product consisting of approximately equal amounts of CPR 3003 and CPR 3004. The two compounds are separated and purified by MPLC, using 800 g silica gel as the stationary phase and $CH_2Cl_2$/$CH_3OH$/HOH (40/15/1.5, v/v/v) as the mobile phase. The yield of pure CPR 3003 and CPR 3004 is on the order of 2.5 g each. The remainder is recovered as a mixture of both compounds which can be rechromatographed for further yields. If CPR 3004 is of primary interest, a 1.5-fold excess of S-methyl-N,N'-ethylene thiourea should be utilized instead of the indicated 4-fold excess.

EXAMPLE 8

By following the procedures outlined in examples 4–7, except that an equivalent amount of each 1-O-R-3-O-trityl-glycerol of Example 3-B is employed as the starting material, the following respective end products of Formula Ia and Formula Ib are obtained: the corresponding 1-O-n-tetradecyl-, 1-O-n-hexadecyl-, 1-O-n-eicosyl-, 1-O-(9-octadecenyl)-, 1-O-(9-hexadecenyl)-, 1-O-(2-chloro-n-octadecyl)-, 1-O-(2-methoxy-n-octadecyl)- and 1-O-(2-cyano-n-hexadecyl)- derivatives of 2-O-methyl-glycero-3-phospho-N-[3-(2-imidazolinyl)-2-imidazolinyl]-ethanolamine (Formula Ia) and 2-O-methyl-glycero-3-phospho-N-(2-imidazolinyl)-ethanolamine (Formula Ib).

EXAMPLE 9

Anti-viral Assay for Herpes Simplex Virus Type 1

1. Buffalo Green Monkey Kidney cells, obtained from Dr. G. Sedmak, City of Milwaukee, Public Health Department Virology Laboratory, are plated at a density of $7 \times 10^4$ cells per well in a standard flat bottom 96 well cell culture plate. The cells are contained in a volume of 200 µl Dulbecco's Modified Eagles Medium (DMEM) containing 10% serum [1:1 mixture of fetal bovine serum and defined supplemented calf serum (Hyclone, Inc., Ogden, Utah), 10 mM HEPES buffer (pH 7.2), 100 U/ml penicillin and 100 µg/ml streptomycin sulfate]. HEPES and antibiotics are obtained from Sigma Chemical Co. (St. Louis, Mo.). Two wells are plated for each of the following samples: compound CPR-3003, cell control (cells only), virus control (cells infected but not treated), vehicle control (solvent for compound, 9:1 dimethylsulfoxide:ethanol), and cell counts.

2. The cultures are incubated at 37° C. with 5% $CO_2$ until a monolayer of cells is formed on the bottom of each well (usually overnight).

3. The media is removed from the wells by aspiration. The cells are refilled with either media containing the desired concentration of test compound CPR-3003 (100 µM final concentration), media only (cell control and virus control samples), or solvent (9:1, DMSO:ethanol) at a final concentration of 0.33%. Compound CPR-3003 is dissolved at a stock concentration of 30 mM and diluted 300-fold. The cell count wells receive media only.

4. The cultures are incubated for 24 hr at 37° C. with 5% $CO_2$.

5. At the end of 24 hr, each well is scored for the presence of toxicity (cells exposed to compound but not infected) as indicated by rounding and/or detachment of the cells from the plate. Scoring is as follows:

1+, ≦25% of cells rounded;

2+, 25 to 50% of cells rounded;

3+, 75% of cells rounded;

4+, 100% of cells rounded.

6. The media is removed from the cell count wells by aspiration. The monolayer is rinsed 2× with 100 µl of trypsin:EDTA solution and is incubated at 37° C. until the cells can be suspended (usually 2–5 minutes). The cells are counted in a hemocytometer to determine the number of cells per well.

7. The remaining wells, except the cell control samples, are infected with 2 plaque forming units per cell of the standard HSV-1 KOS strain of virus using the following procedure. The media is aspirated from the wells. Media (50 µl) with 2% serum containing the desired amount of virus is added to each well. The cultures are then incubated at 37° C. with 5% $CO_2$ for 60 minutes. The plate is gently shaken at 15 to 30 minute intervals to ensure adequate distribution of the virus and exposure of the cells to the virus. At the end of the incubation period, the excess viral solution is removed by aspiration and the cells are refilled (200 µl/well) with either media containing 2% serum (cell control and virus control samples), media containing 2% serum and compound CPR-3003, or media containing the vehicle (solvent control) at the same concentration in the test compound wells.

The plate is incubated at 37° C. with 5% $CO_2$ for 48 hr.

9. At the end of 48 hr, each well is scored for the presence of CPE as indicated by rounding and/or detachment of the cells from the plate. Scoring is as follows:

1+, ≦25% of cells rounded;

2+, 25 to 50% of cells rounded;

3+, 50 to 75% of cells rounded;

4+, 100% of cells rounded.

10. After scoring for viral CPE, the yield of infectious virus in each well is measured by standard plaque assay on Vero cells (available from the American Type Culture Collection (ATCC) under accession no. CCL 81). Virus is released from the cells by freezing and thawing (–80° C. and 37° C.) three times. Serial 10-fold dilutions of each sample are made in media containing 2% serum. Vero cell monolayers of Buffalo Green cells in 96-well cell culture plates ($1 \times 10^6$ cells/well) are infected with 100 µl of each dilution (separate well per dilution). Following a 1 hr adsorption period with gentle rocking at 37° C., the virus inoculum is removed, the monolayer is overlayed with 2 ml of 2% methyl-cellulose in media with 2% serum followed by 2 ml of media with 2% serum. The titer plates are incubated at 37° C. with 5% $CO_2$ until viral plaques become visible (3–4 days). The cells are fixed by adding 2 ml of phosphate buffered saline (PBS) containing 10% (v:v) formalin. The methylcellulose, media and formalin are removed by aspiration. Two mls of PBS-formalin are added and incubated 5 minutes. The fixative is removed and the cells stained with 1% crystal violet in 70% ethanol water (v:v). Excess stain is rinsed from the cells, the number of plaques is counted and the yield of virus in the original sample is calculated.

Table 1 shows the results of the CPE inhibition assay. Exposure of the cells to compound CPR-3003 completely inhibits the development of viral cytopathic effect and is not toxic. The DMSO vehicle used for dissolving the compound is not toxic and does not prevent the development of viral CPE, indicating the vehicle has no antiviral activity. The cell control and virus controls also give the expected results.

Table 1 also shows the data from the yield reduction assay. As expected, the DMSO (vehicle control) has no effect on viral yield ($1 \times 10^6$ pfu/ml) compared to the virus control ($1 \times 10^6$ pfu/ml). In contrast, treatment of the cells with compound CPR-3003 reduces the yield to $2 \times 10^3$. This represents a 500-fold reduction in infectious virus compared to the virus and vehicle control samples and represents a substantial antiviral effect.

TABLE 1

Anti-Herpes Simplex Virus Activity of Compound CPR-3003

| Sample | Toxicity | Viral CPE | Virus Yields PFU/ml | Yield | Fold-Reduction |
|---|---|---|---|---|---|
| Cell Control | N[a] | —[b] | — | — | — |
| Vehicle Control (DMSO/Ethanol) | N | 4+ | $1 \times 10^6$ | 1.00 | 0 |
| Virus Control | — | 4+ | $1 \times 10^6$ | 1.00 | 0 |
| 3003 | N | 0 | $2 \times 10^3$ | 0.002 | 500 |

[a]N = not toxic
[b]Not scored

EXAMPLE 10

Anti-viral Assay for Poliomyelitis Virus Type III

The antiviral effect of Formula I compounds against Poliovirus Type III is demonstrated in a similar assay procedure as described in Example 9. The steps 1 through 10 of Example 9 are followed as described, except for step 7, which is substituted with the following:

7. The cells are then infected. For this study, the Poliomyelitis virus Type III strain is a vaccine strain obtained from Dr. G. Sedmak, City of Milwaukee, Wis., Public Health Department Virology Laboratory. The cells are infected as follows. The medium is aspirated and replaced with 50 µl of medium (2% serum) containing 100 $TCID_{50}$ doses of the Type III polio virus. The cultures are then incubated at 37° C. with 5% $CO_2$ for 60 minutes. The plate is shaken gently at 15 minute intervals to ensure adequate distribution of the virus and exposure of the cells to the virus. At the end of the incubation period, the media containing the virus is removed by aspiration and replaced with 200 µl of media containing compound CPR-3003 (100 µM), or media only (virus control and vehicle control wells). The cell control wells receive media only (no virus).

Table 2 shows the results of the CPE inhibition assay. Exposure of the cells to compound CPR-3003 prevents the development of viral CPE compared to the virus control and vehicle control samples. Some possible cell rounding is noticed, but this is difficult to discern, hence the ±score. The cell control and virus control samples give the expected results. Table 2 also shows the data from the yield reduction assay. Compound CPR-3003 reduces the yield of infectious virus by 100-fold compared to the virus control, which represents a substantial antiviral effect.

TABLE 2

Anti-Poliomyelitis Virus Type III Activity of Compound CPR-3003

| Sample | Toxicity | Viral CPE | Titer (PFU/ml) | Fold-Reduction |
|---|---|---|---|---|
| Cell Control | N[a] | —[b] | — | — |
| Vehicle Control | N | 4+ | ND[c] | ND |
| Virus Control | — | 4+ | $2.9 \times 10^7$ | 0 |
| 3003 | N | ± | $2.8 \times 10^5$ | 100 |

[a]N = Not toxic
[b]Not scored
[c]ND = Not determined

EXAMPLE 11

The following illustrative pharmaceutical compositions are each prepared in the conventional manner:

A. Tablets:

| Ingredients | Per Tablet (mg) |
|---|---|
| CPR-3003 | 50–100 |
| Lactose | 70 |
| Maize starch | 70 |
| Polyvinylpyrrolidone | 5 |
| Magnesium stearate | 5 |
| Tablet weight | 200–250 |

B. An oil-in-water cream base formulation:

| Ingredients | Grams |
|---|---|
| CPR-3004 | 10.0 |
| Anhydrous lanolin | 20.0 |
| Polysorbate 60 | 4.0 |
| Sorbitan monopalmitate | 2.0 |
| Light liquid paraffin | 4.0 |
| Propylene glycol | 5.0 |
| Methyl hydroxybenzoate | 0.1 |
| Purified water, | to 100.0 |

| Ingredients | Amount |
|---|---|

C. Capsules: for 1000 capsules:

| | |
|---|---|
| Active Compound or Salt | 50 g |
| Lactose | 450 g |
| Magnesium Stearate | 5 g |

The ingredients are thoroughly mixed and packed into gelatin capsules.

D. Injection: for 1000 ampules:

| | |
|---|---|
| Active Compound or Salt | 5 g |
| Buffering Agents | q.s. |
| Propylene Glycol | 400 mg |
| Water for injection | 600 ml |

The active compound or salt and buffering agents are dissolved in the propylene glycol at about 50° C. The water for injection is then added with stirring and the resulting solution is filtered, filled into ampules, sealed and sterilized by autoclaving.

I claim:

1. A method of treating a viral infection in a mammal afflicted with same which comprises administering to said mammal an anti-virally effective amount of an N-substituted glycerophosphoethanolamine of Formula I:

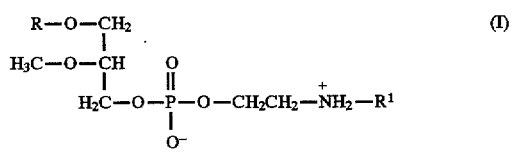

and the isomeric forms thereof; wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and $R^1$ is 3-(2-imidazolinyl)-2-imidazolinyl or 2-imidazolinyl; and the pharmaceutically acceptable salts thereof.

2. The method of claim 1 wherein R is $C_{16-18}$ alkyl and $R^1$ is 3-(2-imidazolinyl)-2-imidazolinyl.

3. The method of claim 1 wherein R is alkyl and $R^1$ is 2-imidazolinyl.

4. The method of claim 1 wherein the compound of Formula I is 1-O-n-octadecyl-2-O-methyl-glycero-3-phospho-N-[3-(2-imidazolinyl)-2-imidazolinyl]-ethanolamine.

5. The method of claim 1 wherein the compound of Formula I is 1-O-n-octadecyl-2-O-methyl-glycero-3-phospho-N-(2-imidazolinyl)-ethanolamine.

6. The method of claim 1 wherein said viral infection is caused by a virus selected from the group consisting of herpes simplex viruses and poliomyelitis viruses.

7. The method of claim 6 wherein said viral infection is caused by a herpes simplex virus.

8. The method of claim 7 wherein said viral infection is caused by herpes simplex virus Type 1.

9. The method of claim 6 wherein said viral infection is caused by a poliomyelitis virus.

10. The method of claim 9 wherein said viral infection is caused by poliomyelitis virus type III.

* * * * *